United States Patent
Qi et al.

(10) Patent No.: US 11,254,715 B2
(45) Date of Patent: Feb. 22, 2022

(54) PROTEIN ASSOCIATED WITH DISEASE RESISTANCE AND ENCODING GENE THEREOF, AND USE THEREOF IN REGULATION OF PLANT DISEASE RESISTANCE

(71) Applicant: Pherobio Technology Co., Ltd., Beijing (CN)

(72) Inventors: Junsheng Qi, Beijing (CN); Zhizhong Gong, Beijing (CN); Xuhui Hong, Beijing (CN)

(73) Assignee: Pherobio Technology Co., Ltd., Beijing (CN)

( * ) Notice: Subject to any disclaimer, the term of this patent is extended or adjusted under 35 U.S.C. 154(b) by 308 days.

(21) Appl. No.: 15/541,551

(22) PCT Filed: Jan. 4, 2016

(86) PCT No.: PCT/CN2016/070035
§ 371 (c)(1),
(2) Date: Jul. 5, 2017

(87) PCT Pub. No.: WO2016/110229
PCT Pub. Date: Jul. 14, 2016

(65) Prior Publication Data
US 2021/0292782 A1 Sep. 23, 2021

(30) Foreign Application Priority Data
Jan. 6, 2015 (CN) .......................... 201510003843.1

(51) Int. Cl.
*C12N 15/82* (2006.01)
*C07K 14/37* (2006.01)
*A01N 63/50* (2020.01)

(52) U.S. Cl.
CPC .............. *C07K 14/37* (2013.01); *A01N 63/50* (2020.01); *C12N 15/8205* (2013.01); *C12N 15/8282* (2013.01)

(58) Field of Classification Search
CPC ................................................ C12N 15/8282
See application file for complete search history.

(56) References Cited

FOREIGN PATENT DOCUMENTS

| CA | 2873360 A1 | 11/2013 |
| CN | 105198967 A | 12/2015 |

OTHER PUBLICATIONS

Bu, Bingwu, et al. "A fungal protein elicitor PevD1 induces Verticillium wilt resistance in cotton." Plant cell reports 33.3 (2014): 461-470. (Year: 2014).*
Wang, Jian-Ying, et al. "VdNEP, an elicitor from Verticillium dahliae, induces cotton plant wilting." Applied and Environmental Microbiology 70.8 (2004): 4989-4995. (Year: 2004).*
Bingwu BU et al., 'A fungal protein elicitor PevD1 induces Verticillium wilt resistance in cotton' Plant Cell Rep, vol. 33, 2014, pp. 461-470.
Search Report for corresponding Chinese Application No. 201510003843.1 dated Feb. 7, 2017 and English translation thereof.
Bing-wu Bu and Xiu-fen Yang, "Cotton Resistance Against verticillium wilt induced by PevD1 and The mechanism thereof," Proceedings of 2012 Academic Annual Conference of Chinese Society for Plant Pathology, Dec. 31, 2017.
Wang, J. et al.: "VdNEP, an Elicitor from Verticillium dahliae, Induces Cotton Plant Wilting. <http://scholar.google.com/scholar?q=>", Applied and Environmental Microbiology, vol. 70, No. 8, Aug. 31, 2004 (Aug. 31, 2004), pp. 4990.
Wang, Bingnan et al.: "Purification and Its Bioassay of Secreted Elicitor Protein from Verticillium dahlia". <http://scholar.google.com/scholar?q=>, Biotechnology Bulletin, Nov. 30, 2011 (Nov. 30, 2011), pp. 166 and-170.
DATABASE GenBank [o] Jan. 30, 2006 (Jan. 30, 2006), Database accession No. AAS45249.
International Search Report PCT/ISA/210 for International Application No. PCT/cn2016/070035 dated Apr. 11, 2016.

* cited by examiner

*Primary Examiner* — Weihua Fan
(74) *Attorney, Agent, or Firm* — Harness, Dickey & Pierce, P.L.C.

(57) ABSTRACT

A protein provided is: a) a protein with an amino acid sequence as shown in amino acids 1-264 of SEQ ID NO: 1; b) a protein that is associated with disease resistance and obtained after an amino acid sequence as shown in amino acids 1-264 of SEQ ID NO: 1 in a Sequence Listing is subjected to substitution and/or deletion and/or addition of one or several amino acid residues; c) a protein with an amino acid sequence as shown in SEQ ID NO: 1; or d) a protein that is associated with disease resistance and obtained after the amino acid sequence as shown in SEQ ID NO: 1 in the Sequence Listing is subjected to substitution and/or deletion and/or addition of one or several amino acid residues. Experiments demonstrate that the protein associated with disease resistance and the encoding gene thereof can be used to enhance plant disease resistance.

15 Claims, 3 Drawing Sheets
Specification includes a Sequence Listing.

SEQUENCE LISTING

<160> NUMBER OF SEQ ID NOS: 16

<210> SEQ ID NO 1
<211> LENGTH: 287
<212> TYPE: PRT
<213> ORGANISM: Artificial sequence
<220> FEATURE:
<223> OTHER INFORMATION: Synthesized Sequence

<400> SEQUENCE: 1

```
Met Leu Ser Leu Gln Thr Ala Ala Leu Leu Leu Phe Pro Leu Val Ala
1               5                   10                  15

Ala Ser Pro Val Ala Arg Ala Ala Glu Thr Ser Val Thr Val Thr Val
                20                  25                  30

Asp Thr Ala Pro Ala Gly Pro Thr Ser Ser Thr Tyr Asn Trp Ala Glu
            35                  40                  45

Gly Trp Lys Ala Asn Phe Pro Ile His Gln Ser Cys Asn Ile Thr Leu
        50                  55                  60

Arg Thr Gln Leu Glu Ala Ala Leu Ala Glu Thr Met Thr Ile Ala Ala
65                  70                  75                  80

His Ala Arg Asp His Leu Leu His Asn Pro Lys Ser Glu Leu Ala Thr
                85                  90                  95

Lys Phe Phe Gly Asn Gln Ser Val Ala Gly Pro Ile Gly Trp Tyr Ser
                100                 105                 110

Lys Val Val Ser Thr Asp Lys Ser Glu Met Leu Phe Arg Cys Asp Asp
            115                 120                 125

Pro Asp Arg Asn Cys Ala Thr Gln Asp Gly Trp Ala Gly His Trp Arg
        130                 135                 140

Gly Ser Asn Ala Thr Gln Glu Thr Val Ile Cys Asp Leu Ser Tyr Glu
145                 150                 155                 160

Ile Arg Arg Pro Leu Ala Ala Leu Cys Gly Gly Gly Tyr Thr Val Ala
                165                 170                 175

Glu Ser Lys Leu Asn Thr Tyr Trp Ala Thr Gly Leu Leu His Arg Ala
            180                 185                 190

Phe His Leu Pro Gly Ile Ser Asp Gly Ile Ile Asp His Tyr Ala Glu
        195                 200                 205

Asp Tyr Ala Glu Ala Leu Lys Leu Ala Ala Thr Glu Pro Glu Leu Ser
    210                 215                 220

Ile Ile Asp Ser Asp Thr Leu Gln Tyr Phe Ala Ile Glu Ala Tyr Ala
225                 230                 235                 240

Tyr Asp Ile Ala Ile Pro Gly Val Gly Cys Pro Gly Glu Ser Pro Ser
                245                 250                 255

Leu Thr Pro Pro Pro Ala Asn Leu Met Asp Tyr Lys Asp His Asp Gly
            260                 265                 270

Asp Tyr Lys Asp His Asp Ile Asp Tyr Lys Asp Asp Asp Asp Lys
        275                 280                 285
```

<210> SEQ ID NO 2
<211> LENGTH: 864
<212> TYPE: dna
<213> ORGANISM: Artificial sequence
<220> FEATURE:
<223> OTHER INFORMATION: Synthesized Sequence

<400> SEQUENCE: 2

```
atgctttctc tccagaccgc agccctgctg ctcttccctc tcgtcgctgc ctctcccgtg    60
gcacgcgctg ctgagaccag tgttaccgtc acggtggaca ctgcccctgc cggccctacc   120
```

-continued

```
agctccacct acaactgggc cgaaggctgg aaggccaact tccccatcca ccagtcttgc      180
aacatcaccc ttcgtactca gctcgaggct gctctcgccg agaccatgac cattgcggcc      240
cacgcccgcg atcatcttct ccacaacccc aagtccgagc tggcgacgaa gttcttcggc      300
aaccagtctg tcgccggccc catcggctgg tactccaagg tcgtctcgac cgacaagtct      360
gagatgctct tccgctgcga cgaccctgat cgtaactgcg ctacccaaga tggctgggcc      420
ggccactggc gcggctcgaa tgccacccag gagacggtca tctgcgacct ctcctacgag      480
atccgccgcc ctcttgccgc tctctgcggt ggtggttata ccgtggccga gtccaagctc      540
aacacctact gggccactgg ccttctgcac cgcgccttcc acctgcccgg catcagcgac      600
ggcatcatcg atcactacgc tgaggattac gccgaggccc tcaagcttgc cgccactgag      660
cctgaactct ccatcatcga cagcgacacc cttcagtact tcgccattga ggcttatgcc      720
tatgacattg ccatccccgg cgtcggctgc cccggcgaga gcccatcatt gacaccgccg      780
ccggcaaatc tcatggacta caaagaccat gatggagact ataaggatca cgacatcgat      840
tacaaggacg atgacgataa gtaa                                             864
```

<210> SEQ ID NO 3
<211> LENGTH: 5
<212> TYPE: PRT
<213> ORGANISM: Artificial sequence
<220> FEATURE:
<223> OTHER INFORMATION: Poly-Arg

<400> SEQUENCE: 3

Arg Arg Arg Arg Arg
1               5

<210> SEQ ID NO 4
<211> LENGTH: 6
<212> TYPE: PRT
<213> ORGANISM: Artificial sequence
<220> FEATURE:
<223> OTHER INFORMATION: Poly-His

<400> SEQUENCE: 4

His His His His His His
1               5

<210> SEQ ID NO 5
<211> LENGTH: 8
<212> TYPE: PRT
<213> ORGANISM: Artificial sequence
<220> FEATURE:
<223> OTHER INFORMATION: FLAG

<400> SEQUENCE: 5

Asp Tyr Lys Asp Asp Asp Asp Lys
1               5

<210> SEQ ID NO 6
<211> LENGTH: 8
<212> TYPE: PRT
<213> ORGANISM: Artificial sequence
<220> FEATURE:
<223> OTHER INFORMATION: Strep-tag II

<400> SEQUENCE: 6

Trp Ser His Pro Gln Phe Glu Lys
1               5

<210> SEQ ID NO 7
<211> LENGTH: 10
<212> TYPE: PRT
<213> ORGANISM: Artificial sequence
<220> FEATURE:
<223> OTHER INFORMATION: c-myc(non)

<400> SEQUENCE: 7

Glu Gln Lys Leu Ile Ser Glu Glu Asp Leu
1               5                   10

<210> SEQ ID NO 8
<211> LENGTH: 20
<212> TYPE: dna
<213> ORGANISM: Artificial sequence
<220> FEATURE:
<223> OTHER INFORMATION: Synthesized Sequence

<400> SEQUENCE: 8 atgctttctctccagaccgc                                                    20

<210> SEQ ID NO 9
<211> LENGTH: 20
<212> TYPE: dna
<213> ORGANISM: Artificial sequence
<220> FEATURE:
<223> OTHER INFORMATION: Synthesized Sequence

<400> SEQUENCE: 9 gagatttgccggcggcggtg                                                    20

<210> SEQ ID NO 10
<211> LENGTH: 21
<212> TYPE: dna
<213> ORGANISM: Artificial sequence
<220> FEATURE:
<223> OTHER INFORMATION: Synthesized Sequence

<400> SEQUENCE: 10 gagatttgccggcggcggtgt                                                   21

<210> SEQ ID NO 11
<211> LENGTH: 17
<212> TYPE: dna
<213> ORGANISM: Artificial sequence
<220> FEATURE:
<223> OTHER INFORMATION: Synthesized Sequence

<400> SEQUENCE: 11 ccctggctgattacatc                                                       17

<210> SEQ ID NO 12
<211> LENGTH: 20
<212> TYPE: dna
<213> ORGANISM: Artificial sequence
<220> FEATURE:
<223> OTHER INFORMATION: Synthesized Sequence

<400> SEQUENCE: 12 tggtgtcagtgggttcaatg                                                    20

<210> SEQ ID NO 13
<211> LENGTH: 23
<212> TYPE: dna
<213> ORGANISM: Artificial sequence
<220> FEATURE:

```
<223> OTHER INFORMATION: Synthesized Sequence

<400> SEQUENCE: 13 atgctttctctccagaccgcagc                                              23

<210> SEQ ID NO 14
<211> LENGTH: 23
<212> TYPE: dna
<213> ORGANISM: Artificial sequence
<220> FEATURE:
<223> OTHER INFORMATION: Synthesized Sequence

<400> SEQUENCE: 14 tagcgcagttacgatcagggtcg                                              23

<210> SEQ ID NO 15
<211> LENGTH: 20
<212> TYPE: dna
<213> ORGANISM: Artificial sequence
<220> FEATURE:
<223> OTHER INFORMATION: Synthesized Sequence

<400> SEQUENCE: 15 gcaacatcaccctttcgtact                                                20

<210> SEQ ID NO 16
<211> LENGTH: 19
<212> TYPE: dna
<213> ORGANISM: Artificial sequence
<220> FEATURE:
<223> OTHER INFORMATION: Synthesized Sequence

<400> SEQUENCE: 16 cagactggttgccgaagaa                                                  19
```

PROTEIN ASSOCIATED WITH DISEASE RESISTANCE AND ENCODING GENE THEREOF, AND USE THEREOF IN REGULATION OF PLANT DISEASE RESISTANCE

CROSS-REFERENCE TO RELATED APPLICATIONS

This application is a national phase under 35 U.S.C. § 371 of PCT International Application No. PCT/CN2016/070035 which has an International filing date of Jan. 4, 2016, which claims priority to Chinese Application No. 201510003843.1, filed Jan. 6, 2015, the entire contents of each of which are hereby incorporated by reference.

INCORPORATION-BY-REFERENCE OF MATERIAL SUBMITTED ON A COMPACT DISC OR AS A TEXT FILE VIA THE OFFICE ELECTRONIC FILING SYSTEM (EFS-WEB)

The contents of the electronic sequence listing (sequence-listing.txt; Size: 6185 bytes; and Date of Creation: Oct. 12, 2020) is hereby incorporated herein by reference in its entirety.

FIELD OF THE INVENTION

The present invention relates to a protein associated with disease resistance, a gene encoding the protein, and use thereof in regulation of plant disease resistance in the field of biotechnology.

BACKGROUND OF THE INVENTION

Cotton is an important cash crop in China, and cotton textiles occupy a pivotal position in China's export trade. *Verticillium* wilt is a most important disease of cotton, with a perennial incidence area of more than three to four million hm$^2$ in China, accounting for more than 70% of an entire cotton field area. This generally causes a cut of 20%-30%, and 60%-70% in heavily infected field, or even failure of the crop. An annual loss of cotton caused by *Verticillium* wilt reaches one million tons, and the quality of cotton fibers severely declines after a disease. At present, China's large-scale planted *Gossypium hirsutum* is difficult to achieve a high level of *Verticillium* wilt resistance. *Gossypium barbadense*, although being resistant to *Verticillium* wilt, cannot be planted in large areas due to low yield, susceptibility to *Fusarium* wilt, requirement for high accumulated temperature, etc. Since 1950, China's cotton breeders have been trying to incorporate disease resistance genes of *Gossypium barbadense* into *Gossypium hirsutum* by crossbreeding, so as to cultivate varieties with high resistance to *Verticillium* wilt and high yield, but all failed. Liu Haiyang et al. (2012) reported that, among 120 varieties in a main cotton planting area and regional trials, only one was between *Verticillium* wilt resistance and disease resistance, and the rest were resistant or susceptible varieties. Therefore, it is necessary to clone a gene associated with disease resistance in *Gossypium barbadense*, and introduce such a gene into high-yield *Gossypium hirsutum* by a genetically modified approach, to cultivate high-yield and *Verticillium dahliae* resistant varieties. This will be of significant importance in increasing cotton production, improving farmers' income, ensuring safety of cotton in China, and promoting development of national economy.

Main pests and diseases of cotton include *Fusarium* wilt, *Verticillium* wilt, and *Helicoverpa armigera*. *Verticillium* wilt has not only a large incidence area, but also an increasing serious illness area. Strong pathogenic defoliating strains especially cause devastating damages, and 71.9% of defoliating strains is strong pathogenic bacteria. Since 1993, *Verticillium* wilt has frequently broken out in China. In 2003, large-scale outbreak of *Verticillium* wilt occurred in China's Yellow River, Yangtze River, and western *Gossypium hirsutum* areas at the same time. In 2006, *Verticillium* wilt attacked Jiluyu (China's Hebei, Shandong, and Henan provinces) severely, and more than 70% of a total planting area of cotton in these provinces were caught by serious disease. Currently, Xinjiang Autonomous Region has become a main producing area of cotton in China, and with popularization of drip irrigation under film, incidences of *Verticillium* wilt are also rapidly increasing.

The occurrence of *Verticillium* wilt not only reduces lint production, but also seriously affects cotton quality. *Verticillium* wilt is usually divided into five grads from Grade 0 to Grade IV, and to measure disease resistance of a variety, a disease index is generally used. Regarding *Verticillium* wilt, disease indexes at 0-10, 11-20, 21-35, and higher than 35 indicate high resistance, disease resistance, tolerance to disease, and susceptibility to disease, respectively. After the cotton is infected, the number of boll setting in individual plant will be significantly reduced due to lack of nutrient supply. When the disease becomes serious, the number of boll setting in individual plant is less than 50% of that on normal conditions (when the number of boll setting in individual plant is about 18). Such being the case, even if the bolls do not fall off, the weight per cotton boll will be significantly reduced. It has been estimated that, the outbreak of *Verticillium* wilt in 2003 reduced lint production by 230 million kilograms, which directly caused economic losses of about RMB 3 billion. After that, *Verticillium* wilt caused more than RMB 1 billion of economic losses each year in China. After being infected, high resistant cotton will suffer significantly deteriorated fiber quality, including reduced general fineness by 20%, decreased strength by 22%, and reduced length by 2 mm. *Verticillium* wilt is caused by *Verticillium* dahlia in China. Once being in the soil, such bacteria will survive more than 20 years. As a result, *Verticillium* wilt has been known as cotton "cancer." *Verticillium* wilt has attracted attention in China in research and control thereof since 1972, but has not yet been effectively controlled so far. Currently, the control of *Verticillium* wilt substantially includes chemical control, biological control, agricultural control, and disease-resistant breeding control. Chemical control has a certain control effect, but also brings about serious pollution to the environment. Biological control, using *Trchoderma* spp., produces a certain control effect, the biocontrol effects of which are, however, largely subject to environmental conditions. And long rotation of agricultural control is difficult to achieve in China. Disease-resistant breeding control, which aims to cultivate disease-resistant varieties, is a most cost-effective approach. Therefore, a most cost-effective solution to a resistant problem of cotton to *Verticillium* wilt is to clone a gene associated with *Verticillium* wilt resistance, cultivate new varieties of cotton by genetically modified approaches, and enhance resistance to *Verticillium* wilt.

The use of a genetically modified approach to create new germplasm resources and cultivate disease-resistant varieties is a most cost-effective approach to control *Verticillium* wilt. *Gossypium barbadense* L., which is highly resistant to *Verticillium* wilt, although containing a gene associated with disease resistance, cannot be planted in a large area due to its low yield. And its resistance gene is difficult to integrate into a genome of *Gossypium hirsutum* by crossbreeding. Therefore, a best solution is to clone a gene associated with *Verticillium* wilt resistance in *Gossypium barbadense*, transform *Gossypium hirsutum* L., and cultivate varieties with high yield and high-resistance to *Verticillium* wilt. Modern molecular genetics facilitates cloning of genes associated with disease resistance. In recent years, researchers at home and abroad have made specific progress in cloning *Verticillium* wilt resistance gene (R gene), transforming broad-spectrum antimicrobial gene, and transforming a *Gossypium barbadense* gene associated with disease resistance. The above study broadens gene sources resistant to *Verticillium* wilt, and lays the foundation for cultivation of genetically modified varieties resistant to *Verticillium* wilt. In addition, in recent years, with the in-depth study of the interaction mechanism between plants and pathogens, it has been found that PTI (PAMP-triggered immunity, a plant immune response induced by extracellular pathogenic factor) and ETI (effector-triggered immunity, an immune response induced by intracellular effector factor) are two modes of triggering immunity of plants. In terms of researches in *Verticillium* wilt, Dutch scientists have first proved that a PTI mechanism can be applied to plant resistance to *Verticillium dahliae*, while the mechanism of intracellular resistance to *Verticillium* wilt has not been reported so far.

SUMMARY OF THE INVENTION

The technical problem to be solved by the present invention is how to enhance disease resistance in plant.

In order to solve the above technical problem, the present invention first provides a protein.

The protein of the present invention, named VdAL, is a protein of a), b), c), or d) as follows:

a) a protein having an amino acid sequence as shown in amino acids 1-264 of SEQ ID NO: 1;

b) a protein that is associated with disease resistance and obtained after an amino acid sequence as shown in amino acids 1-264 of SEQ ID NO: 1 in a Sequence Listing is subjected to substitution and/or deletion and/or addition of one or several amino acid residues;

c) a protein with an amino acid sequence as shown in SEQ ID NO: 1; and d) a protein that is associated with disease resistance and obtained after the amino acid sequence as shown in SEQ ID NO: 1 in the Sequence Listing is subjected to substitution and/or deletion and/or addition of one or several amino acid residues, wherein SEQ ID NO: 1 consists of 287 amino acids, and amino acids 265-287 of SEQ ID NO: 1 exhibit an amino acid sequence of FLAG.

In order to facilitate purification of the protein of a), a tag as shown in Table 1 can be attached to an amino-terminal or a carboxy-terminal of the protein shown in SEQ ID NO: 1 in the Sequence Listing.

TABLE 1

Tags sequences

| Tag | Residue | Sequence |
| --- | --- | --- |
| Poly-Arg | 5-6 (usually 5) | RRRRR (SEQ ID NO: 3) |
| Poly-His | 2-10 (usually 6) | HHHHHH (SEQ ID NO: 4) |
| FLAG | 8 | DYKDDDDK (SEQ ID NO: 5) |

TABLE 1-continued

Tags sequences

| Tag | Residue | Sequence |
| --- | --- | --- |
| Strep-tag II | 8 | WSHPQFEK (SEQ ID NO: 6) |
| c-myc | 10 | EQKLISEEDL (SEQ ID NO: 7) |

VdAL in b) or d) above may be artificially synthesized, or obtained by synthesis of encoding genes thereof and then biological expression. The gene encoding VdAL in b) above can be obtained after the codon(s) of one or several amino acid residues is deleted from the DNA sequence shown in nucleotides 1-792 of SEQ ID NO: 2 in the Sequence Listing, and/or after missense mutation of one or several base(s) therein, and/or after an encoding sequence of the tag as shown in Table 1 is attached to a 5' end and/or 3' end thereof.

In order to solve the above technical problem, the present invention further provides a biomaterial comprising the VdAL.

The biomaterial provided by the present invention in connection with the VdAL is any one selected from a group consisting of B1) to B22) as follows:

B1) a nucleic acid molecule encoding the VdAl;

B2) an expression cassette comprising the nucleic acid molecule of B1);

B3) a recombinant vector comprising the nucleic acid molecule of B1);

B4) a recombinant vector comprising the expression cassette of B2);

B5) a recombinant microorganism comprising the nucleic acid molecule of B1);

B6) a recombinant microorganism comprising the expression cassette of B2);

B7) a recombinant microorganism comprising the recombinant vector of B3);

B8) a recombinant microorganism comprising the recombinant vector of B4);

B9) a genetically modified plant cell line comprising the nucleic acid molecule of B1);

B10) a genetically modified plant cell line comprising the expression cassette of B2);

B11) a genetically modified plant cell line comprising the recombinant vector of B3);

B12) a genetically modified plant cell line comprising the recombinant vector of B4);

B13) a genetically modified plant tissue comprising the nucleic acid molecule of B1);

B14) a genetically modified plant tissue comprising the expression cassette of B2);

B15) a genetically modified plant tissue comprising the recombinant vector of B3);

B16) a genetically modified plant tissue comprising the recombinant vector of B4);

B17) a genetically modified plant organ comprising the nucleic acid molecule of B1);

B18) a genetically modified plant organ comprising the expression cassette of B2);

B19) a genetically modified plant organ comprising the recombinant vector of B3);

B20) a genetically modified plant organ comprising the recombinant vector of B4);

B21) a genetically modified plant comprising the nucleic acid molecule of B1); and B22) a genetically modified plant comprising the expression cassette of B2).

In the above biomaterial, the nucleic acid molecule of B1) is a gene represented by:

1) a cDNA or DNA molecule with a nucleotide sequence as shown in nucleotides 1-792 of SEQ ID NO: 2 in the Sequence Listing;

2) a cDNA or DNA molecule that exhibits 75% or more identity to the nucleotide sequence defined in 1) and encodes the VdAl;

3) a cDNA or DNA molecule that hybridizes, under stringent conditions, with the nucleotide sequence defined in 1) and encodes the VdAl;

4) a cDNA or DNA molecule with a nucleotide sequence as shown in SEQ ID NO: 2 in the Sequence Listing;

5) a cDNA or DNA molecule that exhibits 75% or more identity to the nucleotide sequence defined in 4) and encodes the VdAl; or 6) a cDNA or DNA molecule that hybridizes, under stringent conditions, with the nucleotide sequence defined in 4) and encodes the VdAl.

The nucleic acid molecule may be DNA, such as cDNA, genomic DNA, and recombinant DNA. Or alternatively, the nucleic acid molecule may also be RNA, such as mRNA and hnRNA.

SEQ ID NO: 2 consists of 864 nucleotides encoding the amino acid sequence shown in SEQ ID NO: 1. Nucleotides 793-864 of SEQ ID NO: 2 encode the FLAG shown in amino acids 265-287 of SEQ ID NO: 1; and nucleotides 1-792 of SEQ ID NO: 2 encode the protein shown in amino acids 1-264 of SEQ ID NO: 1.

One of ordinary skill in the art can readily allow mutation of a nucleotide sequence encoding the VdAL of the present invention, using known approaches, such as directed evolution and point mutation. Those nucleotides that have been artificially modified and exhibit 75% or more identity to the nucleotide sequence of the VdAL isolated in the present invention, as long as they encode the VdAL and have a function of the VdAL, are all nucleotide sequences derived from the present invention and equivalent to the sequence of the present invention.

As used herein, the term "identity" refers to sequence similarity to a natural nucleic acid sequence. "Identity" means that a nucleotide sequence has the similarity of 75% or more, 85% or more, 90% or more, or 95% or more to the nucleotide sequence encoding the protein consisting of the amino acid sequence shown in SEQ ID NO: 1 or in amino acids 1-264 of SEQ ID NO: 1 of the present invention. Identity can be evaluated with naked eyes or computer software. When the computer software is used, identity between two or more sequences can be expressed as a percentage (%), which can be used to evaluate identity between relevant sequences.

In the above biomaterial, the stringent conditions include hybridization at 68° C. in a 2×SSC buffer with 0.1% SDS, followed by washing the membrane twice for 5 min each, and then hybridization at 68° C. in a 0.5×SSC buffer with 0.1% SDS, followed by washing the membrane twice for 15 min each; or alternatively hybridization at 65° C. in a 0.1×SSPE (or 0.1×SSC) buffer with 0.1% SDS, followed by washing the membrane.

The above 75% or more identity can be 80%, 85%, 90%, 95% or more identity.

In the above biomaterial, the expression cassette (VdAL gene expression cassette) of B2) comprising the nucleic acid molecule encoding the VdAL refers to a DNA capable of expressing the VdAL in a host cell. The DNA may include not only a promoter that initiates the transcription of VdAL gene, but may also include a terminator that terminates the transcription of VdAL gene. The expression cassette may further comprise an enhancer sequence. Promoters that can be used in the present invention include, but are not limited to, constitutive promoters, tissues, organs, and development-specific promoters, and inducible promoters. Examples of the promoters include, but are not limited to, constitutive promoter 35S of cauliflower mosaic virus, trauma-induced promoters from tomatoes, leucine aminopeptidase ("LAP," Chao et al. (1999) *Plant Physiol* 120: 979-992); chemically induced promoters from tobacco, pathogenesis-related protein 1 (PR1) (induced by salicylic acid and BTH (benzothiadiazole-7-thiohydroxy acid S-methyl ester)); tomato protease inhibitor II (PIN2) promoter or LAP promoter (all can be induced with methyl jasmonate); heat shock promoter (U.S. Pat. No. 5,187,267); tetracycline-inducible promoter (U.S. Pat. No. 5,057,422); seed-specific promoters, such as millet seed-specific promoter pF128 (CN 101063139B (with a filing number of CN 200710099169.7), seed storage protein-specific promoters (e.g., cabbage, napin, oleosin, and soybean beta conglycin promoters (Beachy et al. (1985) *EMBO J.* 4: 3047-3053)). They can be used alone or in combination with other plant promoters. All references cited are incorporated herein by reference in their entireties. Suitable transcription terminators include, but are not limited to, *Agrobacterium* nopaline synthetase terminator (NOS terminator), cauliflower mosaic virus (CaMV) 35S terminator, tml terminator, pea rbcS E9 terminator, and nopaline and octopine synthase terminator (see, e.g., Odell et al. (I$^{958}$) *Nature*, 313: 810; Rosenberg et al. (1987) *Gene*, 56: 125; Guerineau et al. (1991) *Mol. Gen. Genet*, 262: 141; Proudfoot (1991) *Cell*, 64: 671; Sanfacon et al. *Genes Dev.*, 5: 141; Mogen et al. (1990) *Plant Cell*, 2: 1261; Munroe et al. (1990) *Gene*, 91: 151; Ballad et al. *Nucleic Acids Res.*, 17: 7891; and Joshi et al. (1987) *Nucleic Acid Res.*, 15: 9627).

An existing expression vector can be used to construct the recombinant vector containing the expression cassette of VdAL gene. The plant expression vector can be binary *Agrobacterium tumefaciens* vectors, a vector that can be used for microprojectile bombardment in plant, and the like, such as pAHC25, pBin438, pCAMBIA1302, pCAMBIA2301, pCAMBIA1301, pCAMBIA1300, pBI121, pCAMBIA1391-Xa, and pCAMBIA1391-Xb (CAMBIA). The plant expression vector may also comprise a 3'-untranslated region of a foreign gene, i.e., a polyadenylation signal and any other DNA fragment involved in mRNA processing or gene expression may be comprised. The polyadenylation signal can lead polyadenylation to a 3'-end of an mRNA precursor. For example, plasmid gene induced by *Agrobacterium* crown gall (Ti) (such as nopaline synthase gene Nos), and 3'-end transcribed, untranslated regions of the plant gene (such as soy storage protein gene) all have a similar function. When the gene of the present invention is used to construct a plant expression vector, enhancers, including translation enhancers or transcriptional enhancers, may also be used. Enhancer regions, which may be ATG initiation codon, contiguous region initiation codon, or the like, must be identical to a reading frame of the encoding sequence, so as to ensure correct translation of an entire sequence. The translation control signal and the initiation codon, which have a wide variety of sources, may be either natural or synthetic. The translation initiation region may be derived from a transcription initiation region or a structural gene. In order to facilitate identification and screening of the genetically modified plant cells or plants, a plant expression vector used can be processed through, e.g., addition of a gene that can be expressed in a plant and can encode an enzyme producing a color or synthetise a luminescent compound (such as a GUS gene and a luciferase gene), an antibiotic marker gene (such as a nptII gene that confers resistance to kanamycin and related antibiotics, a bar gene that confers resistance to herbicide phosphinothricin, a hph gene that confers resistance to antibiotic hygromycin, a dhfr gene that confers resistance to methotrexate, and an EPSPS gene that confers resistance to glyphosate), an anti-chemical reagent marker gene (such as a herbicide-resistant gene), or a mannose-6-phosphate isomerase gene that provides the ability of mannose metabolism. For safety of the genetically modified plants, they can be transformed directly by adversity screening without any selective marker gene.

In the above biomaterial, the vector may be a plasmid, cosmid, phage, or viral vector.

In the above biomaterial, the microorganism may be yeast, bacteria, algae, or fungi, such as *Agrobacterium*.

In the above biomaterial, the genetically modified plant organ may be a seed of a genetically modified plant. The genetically modified plant (e.g., maize) may include a seed, a calli, an intact plant, and a cell. The genetically modified maize may include a seed, a calli, an intact plant, and a cell.

In one embodiment of the present invention, the gene encoding the VdAL (i.e., the DNA molecule represented by nucleotides 1-792 of SEQ ID NO: 2) is introduced into *Agrobacterium tumefaciens* GV3101 via a recombinant vector containing an expression cassette of the gene encoding the VdAL. The recombinant vector is recombinant vector pSPT01-VdAL obtained by replacement of a fragment between recognition sites of Sal I and Kpn I in pSPT01 with the DNA molecule shown by the nucleotides 1-792 of SEQ ID NO: 2. pSPT01-VdAL expresses the VdAL protein shown in SEQ ID NO: 1.

In another embodiment of the present invention, the gene encoding the VdAL (i.e., the DNA molecule represented by nucleotides 1-792 of SEQ ID NO: 2) is introduced into *Agrobacterium tumefaciens* GV3101 via a recombinant vector containing an expression cassette of the gene encoding the VdAL. The recombinant vector is recombinant vector pCAMBIA1300-Super-VdAL obtained by replacement of a fragment between recognition sites of Pst I and Kpn I in pCAMBIA1300-Super with the DNA molecule shown by the nucleotides 1-792 of SEQ ID NO: 2. pCAMBIA1300-Super-VdAL expresses the VdAL protein shown in SEQ ID NO: 1.

In order to solve the above technical problem, the present invention further provides use of the VdAL or the biomaterial in:

a) regulation of plant disease resistance; or b) cultivation of a disease-resistant genetically modified plant.

In the above use, the plant may be a dicotyledonous or monocotyledonous plant.

In the above use, the disease resistance may be *Verticillium* wilt resistance.

In the above use, the plant may be a dicotyledonous plant or a monocotyledonous plant; and the disease resistance may be *Verticillium* wilt resistance.

In the above use, the dicotyledonous plant may be the plant of *Gossypium*. The plant of *Gossypium* may be cotton. The cotton may be specifically sGK9708-41.

In order to solve the above technical problem, the present invention further provides a method for cultivating a disease-resistant genetically modified plant.

The method for cultivating a disease-resistant genetically modified plant provided in the present invention comprises a step of introducing a gene encoding the VdAL into a recipient plant, to obtain the disease-resistant genetically modified plant having higher disease resistance than the recipient plant.

In the above method, the gene encoding the VdAL may be a DNA molecule with an encoding sequence as shown in nucleotides 1-792 of SEQ ID NO: 2 in the sequence listing.

In the above method, the plant may be a dicotyledonous plant and/or a monocotyledonous plant.

In the above method, the disease resistance may be *Verticillium* wilt resistance.

In the above method, the gene encoding the VdAL may be a DNA molecule with an encoding sequence as shown in nucleotides 1-792 of SEQ ID NO: 2 in the Sequence Listing; and the plant may be a dicotyledonous plant and/or a monocotyledonous plant.

In the above method, the gene encoding the VdAL may be a DNA molecule with an encoding sequence as shown in nucleotides 1-792 of SEQ ID NO: 2 in the Sequence Listing; and the disease resistance may be *Verticillium* wilt resistance.

In the above method, the plant may be a dicotyledonous plant and/or a monocotyledonous plant; and the disease resistance may be *Verticillium* wilt resistance.

In the above method, the gene encoding the VdAL may be a DNA molecule with an encoding sequence as shown in nucleotides 1-792 of SEQ ID NO: 2 in the Sequence Listing; the plant may be a dicotyledonous plant and/or a monocotyledonous plant; and the disease resistance may be *Verticillium* wilt resistance.

In the above method, the gene encoding the VdAL may also be a DNA molecule with an encoding sequence as shown in SEQ ID NO: 2 in the Sequence Listing.

In the above method, the dicotyledonous plant may be the plant of *Gossypium*. The plant of *Gossypium* may be cotton. The cotton may be specifically sGK9708-41.

In an embodiment of the present invention, the gene encoding the VdAL (i.e., the DNA molecule shown in SEQ ID NO: 2) is introduced into a target plant via a VdAL gene recombinant expression vector containing a VdAL gene expression cassette.

In the above method, the VdAL gene may be first modified as follows and then introduced into a recipient seed plant, so as to achieve a better expression effect.

At the outset, modification and optimization can be performed according to actual requirements, so as to enable efficient expression of the gene. For example, depending on a preferred codon of the recipient plant, the codon of the VdAL gene of the present invention may be altered while the amino acid sequence thereof is maintained, so as to conform to preference of the plant. In an optimization procedure, it is desirable to maintain a certain GC content in an optimized encoding sequence, so as to best achieve a high level expression of an introduced gene in the plant, wherein the GC content may be 35%, more than 45%, more than 50%, or more than about 60%.

Besides, a gene sequence adjacent to a start-methionine can be modified, to enable effective starting of translation. For example, an effective sequence known in the plant can be used for the modification.

Moreover, ligation to expression promoters of various plants can be performed to facilitate expression of the VdAL gene in plants. The promoters may include constitutive, inducible, timing regulation, developmental regulation, chemical regulation, tissue optimization, and tissue-specific promoters. Selection of a promoter varies with requirements in expression time and space, and also depends on a target species. For example, a specific expression promoter of a tissue or organ depends on what development period a receptor is required. Although it has been proved that many promoters derived from dicotyledonous plants are functional in monocotyledonous plants, and vice versa, it is desirable to select dicotyledon promoters for expression in dicotyledonous plants, and monocotyledon promoters for expression in monocotyledonous plants.

In addition, ligation to a suitable transcription terminator can also be performed to improve the expression efficiency of the gene of the present invention, such as tml derived from CaMV and E9 derived from rbcS. Any available terminator known to function in a plant may be ligated to the gene of the present invention.

Furthermore, an enhancer sequence, such as an intron sequence (e.g., from Adhl or bronzel) and a viral leader sequence (e.g., from TMV, MCMV, or AMV) can be introduced.

The recombinant expression vector having VdAL gene can be introduced into a plant cell by a conventional biotechnological means such as Ti plasmid, plant virus vector, direct DNA conversion, microinjection, and electroporation (Weissbach, 1998, "Method for Plant Molecular Biology VIII," Academy Press, New York, pp. 411-463; Geiserson and Corey, 1998, *Plant Molecular Biology* (2nd Edition)).

In the above method, the genetically modified plant is understood to include not only a first-generation genetically modified plant obtained by conversion of a target plant by the VdAL gene, but also a progeny thereof. Regarding a genetically modified plant, a gene can be propagated in the species of the genetically modified plant, and can also be transferred into other varieties of the same species, especially commercial varieties, through a conventional breeding technical means. The genetically modified plant can be a seed, a callus, an intact plant, or a cell.

In order to solve the above technical problem, the present invention further provides a product for regulation of plant disease resistance.

The product for regulation of plant disease resistance provided in the present invention comprises the VdAL or the biomaterial.

An active ingredient of the product for regulation of plant disease resistance may be the VdAL or the biomaterial.

The product for regulation of plant disease resistance can be prepared by the steps of:

cultivating the recombinant microorganism, to express the encoding gene and obtain a recombinant microbial culture expressing the VdAL; and breaking a thallus in the microbial culture, to obtain a biological agent.

In order to solve the above technical problem, the present invention further provides use of the product in regulation of plant disease resistance.

In the above use, the plant is a dicotyledonous plant and/or monocotyledonous plant. The dicotyledonous plant may be the plant of *Gossypium*. The plant of *Gossypium* may be cotton. The cotton may be specifically sGK9708-41.

In the present invention, *Verticillium* wilt may be a disease caused by strain $V_{991}$.

DETAILED DESCRIPTION OF THE EMBODIMENTS

Figure 1:
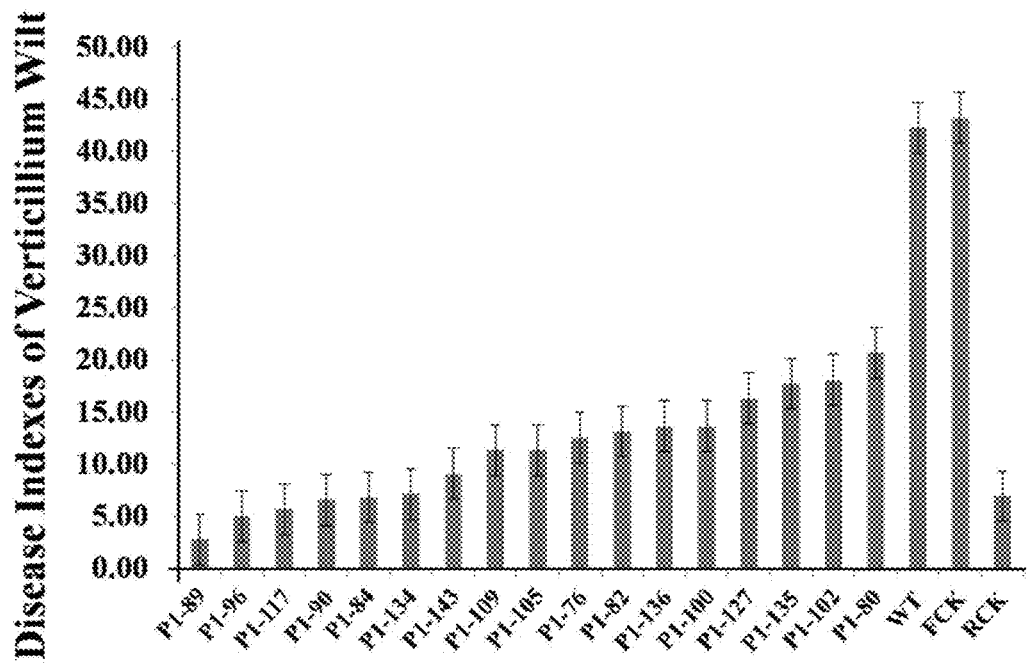
FIG. 1 shows disease indexes of *Verticillium* wilt of some genetically modified cotton lines containing VdAL, wherein WT, FCK, and RCK represent sGK9708-41, SCRC28, and GK44, respectively.

The present invention will be described in further detail with reference to specific examples, which are provided for illustration of the present invention only, but not intended to limit the scope of the present invention.

Experimental approaches indicated in the following examples are conventional approaches, unless otherwise specified.

Materials, reagents, and the like used in the following examples are all commercially available, unless otherwise specified.

*Verticillium* dahlia in the following examples refers to strain $V_{99}1$ (Qi Junsheng & Li Huaifang, "A New Detection Method of Wilting Induction by Phytotoxin from *V. dahliae* on Cotton through Leaf Pricking and Spreading," Cotton Science, 2016, 18 (4): 228-232), which can be obtained by the public from the China Agricultural University (i.e., Applicant). This biomaterial can be used only for the purpose of repeating related experiments of the present invention and cannot be used for other purposes.

GK44 used in the following examples is a product of Shandong Jinqiu Seed Industry Co., Ltd.

SCRC28 used in the following examples is a product of Shandong Nongxing Seed Industry Co., Ltd.

sGK9708-41 used in the following examples is a product of Xinjiang Cotton-Seed Industry Co., Ltd.

*Arabidopsis thaliana* Col used in the following examples is a product of Salk Institute for Biological Studies.

Vector pSPT01 used in the following examples is pSPT01 in Example 1 of Chinese patent application No. 201010521702.6 (published as CN 101962658 A). pSPT01 is built on the basis of pCambia1300, wherein a promoter of a target gene is a super promoter added with a Flag sequence after the promoter, and a reporter gene is replaced with a tfdA gene.

Vector pCAMBIA1300-Super used in the following examples is pCAMBIA1300-Super in Example 1 of Chinese patent application No. 201010521702.6 (publication as CN 101962658 A). pCAMBIA1300-Super is a vector obtained after promoter CaMV35S in pCAMBIA1300 (GenBank of which is FJ362601.1) is replaced with a super strong promoter, and a restriction enzyme cutting site in pCAMBIA1300 is modified.

*Agrobacterium tumefaciens* GV3101 used in the following examples is a product of Beijing Jiuzhou Tian Rui Technology Co., Ltd.

Example 1

In this example, it was proved that protein VdAL associated with disease resistance could enhance disease resistance of cotton.

I. Construction of the Genetically Modified Cotton Containing VdAL

Procedure 1 Constructions of a Recombinant Vector and a Recombinant Strain

A DNA molecule shown in nucleotides 1-792 of SEQ ID NO: 2 in the Sequence Listing, i.e., VdAL protein gene associated with disease resistance, was artificially synthesized. A sequence between recognition sites of Sal I and Kpn I of vector pSPT01 was replaced with the DNA molecule shown in nucleotides 1-792 of SEQ ID NO: 2 in the Sequence Listing (i.e., the VdAL protein gene associated with disease resistance), and other sequences of pSPT01 remained unchanged, to obtain a recombinant vector named pSPT01-VdAL. Recombinant vector pSPT01-VdAL expresses the VdAL protein associated with disease resistance shown in SEQ ID NO: 1 in the Sequence Listing.

SEQ ID NO: 2 consists of 864 nucleotides, encoding an amino acid sequence shown in SEQ ID NO: 1. Nucleotides 793-864 of SEQ ID NO: 2 encode FLAG shown in amino acids 265-287 of SEQ ID NO: 1; and nucleotides 1-792 of SEQ ID NO: 2 encode a protein shown in amino acids 1-264 of SEQ ID NO: 1.

pSPT01-VdAL was introduced into *Agrobacterium tumefaciens* GV3101, to obtain a recombinant strain, which was named A-pSPT01-VdAL.

pSPT01 was introduced into *Agrobacterium tumefaciens* GV3101, to obtain a recombinant strain with an empty vector, and the resulting recombinant strain was named A-pSPT01.

Procedure 2 Construction of disease resistance related VdAL protein genetically modified cotton In step (1), A-pSPT01-VdAL of procedure 1 was streaked on a YEB solid medium containing kanamycin with a final concentration of 50 μg/mL and rifampicin with a final concentration of 50 μg/mL, activated, and cultured for 48 h at 28° C., to obtain single colonies.

In step (2), some single colonies obtained in step (1) were selected and added into a 5 mL of YEB liquid medium containing kanamycin with a final concentration of 50 μg/mL and rifampicin with a final concentration of 50 μg/mL, and shaken for 12 h at 28° C., to obtain a bacterial solution.

In step (3), 2 mL of the bacterial solution obtained in step (2) was connected to a 500 mL of YEB liquid medium containing kanamycin with a final concentration of 50 μg/mL and rifampicin with a final concentration of 50 μg/mL, shaken on a shaking table at 28° C., and cultured to OD600=0.8-1.0, to obtain a bacterial solution.

In step (4), the bacterial solution obtained in step (3) was centrifuged at 4000 rpm for 10 minutes at room temperature, to obtain a bacterial precipitate.

In step (5), the bacterial precipitate obtained in step (4) was re-suspended in 200 mL of ½ MS solution, in which 15 μL of Silwet-77 was added, followed by homogeneous mixing, to obtain an *Agrobacterium tumefaciens* infection solution.

In step (6), buds of a cotton variety sGK9708-41 (2,4-D sensitive line) were isolated by being bagged. The *Agrobacterium tumefaciens* infection solution of step (5) was sprayed on the bagged buds next day during a period from 8 to 9 o'clock. The buds sprayed with the *Agrobacterium tumefaciens* infection solution were then bagged to avoid light, and transformed buds were marked with red ropes. This line was then a genetically modified line of $T_0$ generation. This genetically modified line was passaged to T4 generation (by selfing in each generation). Each generation was screened with 2,4-D, to obtain the following the genetically modified cotton lines of the T4 generation: P1-89, P1-96, P1-117, P1-90, P1-84, P1-134, P1-143, P1-109, P1-105, P1-76, P1-82, P1-136, P1-100, P1-127, P1-135, P1102, P1-80, P1-104, P1-69, P1-110, P1-125, and P1-111, containing VdAL.

In step (7), the VdAL gene in the VdAL genetically modified cotton lines of the T4 generation obtained in step (6) was identified at a genomic level. Cotton variety sGK9708-41 was used as a wildtype reference, with a primer pair of ATGCTTTCTCTCCAGACCGC (SEQ ID NO: 8) and GAGATTTGCCGGCGGCGGTG (SEQ ID NO: 9). Results showed that PCR products of the genetically modified cotton lines, containing VdAL, of the T4 generation obtained in step (6) each had target bands of size 792 bp, indicating that the genetically modified cotton lines, containing VdAL, of the T4 generation obtained in step (6) each had the VdAL gene.

In step (8), expression of the VdAL gene in the genetically modified cotton lines, containing VdAL, of the T4 generation obtained in step (6) was identified by semi-quantitative PCR. Cotton variety sGK9708-41 was used as a wildtype reference, with a primer pair of ATGCTTTCTCTCCAGACCGC (SEQ ID NO: 8) and GAGATTTGCCGGCGGCGGTGT (SEQ ID NO: 10). UBQ was used as an internal reference, with a primer pair of CCCTGGCTGATTACATC (SEQ ID NO: 11) and TGGTGTCAGTGGGTTCAATG (SEQ ID NO: 12). Results showed that PCR products of the genetically modified cotton lines, containing VdAL, of the T4 generation each had the target bands, indicating that the genetically modified cotton lines, containing VdAL, of the T4 generation obtained in step (6) each expressed the VdAL gene.

In step (9), expression of VdAL protein in the genetically modified cotton lines, containing VdAL, of the T4 generation obtained in step (6) was identified by western-blot. Cotton variety sGK9708-41 was used as a wildtype reference. Antibody flag (item number AB003-01A, a product of Shanghai Nearshore Technology Co. LTD/Sinobio Biotech Co., Ltd.) was used. Protein was labeled with a Ponceau S dyeing solution, and a loading amount thereof was adjusted, to enable a same total amount of protein in different lanes. Results were shown in FIG. 5. The results indicated that the genetically modified cotton lines, containing VdAL, of the T4 generation obtained in step (6) each expressed the VdAl protein.

A-pSPT01-VdAL was replaced with A-pSPT01 according to steps (1) to (6), and other steps were unchanged. Genetically modified cotton containing the empty vector was obtained and named genetically modified cotton containing empty-vector.

II. Identification of disease resistance of the genetically modified cotton containing VdAL The genetically modified cotton containing VdAL was inoculated with *Verticillium dahliae*, and disease resistance of a plant after inoculation was evaluated in terms of *Verticillium* wilt index and the number of boll setting in individual plant thereof. The experiment was repeated three times, including the following specific steps each time.

Cotton *Verticillium dahliae* was inoculated into a disease nursery in a field of Shandong Province, to obtain a disease nursery homogeneously distributed with $V_{99}1$ strains. Genetically modified cotton lines P1-89, P1-96, P1-117, P1-90, P1-84, P1-134, P1-143, P1-109, P1-76, P1-82, P1-136, P1-100, P1-127, P1-135, P1-102, P1-80, P1-104, P1-69, P1-110, and P1-111, containing VdAL, and the genetically modified cotton containing empty-vector obtained above, cotton variety sGK9708-41, *Verticillium* wilt resistant cotton variety GK44, and high-yield cotton variety SCRC28 were planted in the above disease nursery, respectively, 30 plants for each line.

Incidence of cotton was graded as follows during a boll stage thereof, and *Verticillium* wilt disease index and relative control effect of cotton were calculated (see Table 2 and FIG. 1):

Grade 0: no diseased leaves;
Grade I: 0.1%-25% of diseased leaves;
Grade II: 25% (excluded)-50% of diseased leaves;
Grade III: 50% (excluded)-75% of diseased leaves; and
Level IV: more than 75% of diseased leaves.

Disease index=(1×Grade *I*plant number+2×Grade *II*plant number+3×Grade *III*plant number+4× Grade *IV*plant number)/(4×*a* total plant number investigated)×100.

Relative control effect (%)=(disease index of *sGK*9708-41–disease index of genetically modified cotton containing VdAL)/disease index of *sGK*9708-41×100%

(the relative control effect of sGK9708-41 was defined to be 0).

Figure 2:
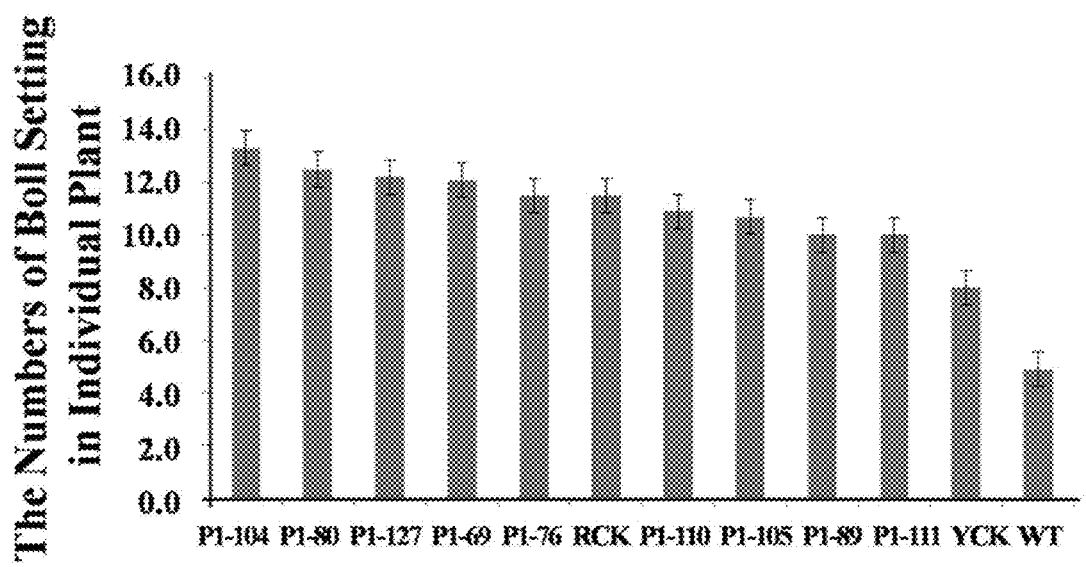
FIG. 2 shows the numbers of boll setting in individual plant of some genetically modified cotton lines containing VdAL, wherein WT, YCK, and RCK represent sGK9708-41, SCRC28, and GK44, respectively.

The numbers of boll setting in individual plant of cotton was counted at the end of the boll stage. The results were shown in Table 3 and FIG. 2.

TABLE 2

Verticillium wilt disease index and relative control effect of the genetically modified cotton containing VdAL

| Line/Variety | disease indexes of Verticillium wilt | Relative control effect (%) |
|---|---|---|
| P1-89 | 2.78 ± 1.00 | 93 |
| P1-96 | 5.00 ± 0.58 | 88 |
| P1-117 | 5.68 ± 0.58 | 86 |
| P1-90 | 6.58 ± 1.41 | 84 |
| P1-84 | 6.82 ± 0.50 | 83 |
| P1-134 | 7.14 ± 3.00 | 83 |
| P1-143 | 9.09 ± 1.00 | 78 |
| P1-109 | 11.36 ± 1.29 | 73 |
| P1-76 | 12.50 ± 1.05 | 70 |
| P1-82 | 13.16 ± 2.50 | 68 |
| P1-136 | 13.64 ± 2.16 | 67 |
| P1-100 | 13.64 ± 0.50 | 67 |
| P1-127 | 16.30 ± 2.06 | 61 |
| P1-135 | 17.71 ± 1.71 | 58 |
| P1-102 | 18.06 ± 1.26 | 57 |
| P1-80 | 20.26 ± 2.45 | 51 |
| P1-104 | 22.83 ± 4.24 | 45 |
| P1-69 | 29.41 ± 0.00 | 30 |
| P1-110 | 27.63 ± 0.96 | 34 |
| P1-111 | 26.67 ± 1.50 | 36 |

TABLE 2-continued

Verticillium wilt disease index and relative control effect of the genetically modified cotton containing VdAL

| Line/Variety | disease indexes of Verticillium wilt | Relative control effect (%) |
|---|---|---|
| Genetically modified cotton containing empty-vector | 43.78 ± 2.54 | −4 |
| sGK9708-41 | 42.19 ± 0.95 | 0 |
| GK44 | 7.61 ± 0.71 | 82 |
| SCRC28 | 43.36 ± 1.04 | −3 |

The results showed that cotton variety sGK9708-41 had no substantial differences from the genetically modified cotton containing empty-vector in terms of *Verticillium* wilt index. *Verticillium* wilt indexes of the genetically modified cotton lines containing VdAL were each lower than the *Verticillium* wilt index of wildtype cotton variety sGK9708-41, and also each lower than the *Verticillium* wilt index of high-yield cotton variety SCRC28. The *Verticillium* wilt indexes of some lines (such as P1-89, P1-96, P1-117, P1-90, P1-84, and P1-134) were each lower even than the *Verticillium* wilt index of *Verticillium* wilt resistant cotton variety GK44. The relative control effect of cotton variety sGK9708-41 had no substantial differences from the relative control effect of the genetically modified cotton containing empty-vector. The relative control effects of the genetically modified cotton lines containing VdAL were each higher than the relative control effect of wild-type cotton variety sGK9708-41, and also higher than the relative control effect of high-yield cotton variety SCRC28. The relative control effects of some lines (such as P1-89, P1-96, P1-117, P1-90, P1-84, and P1-134) each reached above 80%, even higher than the relative control effect of *Verticillium* wilt resistant cotton variety GK44.

The results showed that the VdAL of the present invention could enhance *Verticillium* wilt resistant ability in a plant.

TABLE 3

The numbers of boll setting in individual plant of the genetically modified cotton containing VdAL

| Line/Variety | the Numbers of Boll Setting in Individual plant | Multiple relationship with sGK9708-41 |
|---|---|---|
| P1-89 | 10.3 ± 1.91 | 2.71 |
| P1-96 | 12.5 ± 1.00 | 2.55 |
| P1-117 | 12.2 ± 1.21 | 2.49 |
| P1-90 | 9.4 ± 1.32 | 1.92 |
| P1-84 | 8.9 ± 1.10 | 1.82 |
| P1-134 | 6.7 ± 0.89 | 1.37 |
| P1-143 | 10.2 ± 0.78 | 2.08 |
| P1-109 | 9.3 ± 1.12 | 1.90 |
| P1-105 | 10.7 ± 0.99 | 2.18 |
| P1-76 | 11.5 ± 1.13 | 2.35 |
| P1-82 | 12.1 ± 0.57 | 2.47 |
| P1-136 | 8.8 ± 1.31 | 1.80 |
| P1-100 | 13.1 ± 1.16 | 2.67 |
| P1-127 | 12.2 ± 1.30 | 2.49 |
| P1-135 | 9.1 ± 2.00 | 1.86 |
| P1-102 | 11.9 ± 0.30 | 2.43 |
| P1-80 | 12.5 ± 1.23 | 2.55 |
| P1-104 | 13.3 ± 0.95 | 2.71 |

TABLE 3-continued

The numbers of boll setting in individual plant of the genetically modified cotton containing VdAL

| Line/Variety | the Numbers of Boll Setting in Individual plant | Multiple relationship with sGK9708-41 |
|---|---|---|
| P1-69 | 12.1 ± 1.41 | 2.47 |
| P1-110 | 10.9 ± 0.59 | 2.22 |
| P1-111 | 10 ± 1.11 | 2.04 |
| Genetically modified cotton containing empty-vector | 4.1 ± 1.18 | 0.84 |
| sGK9708-41 | 4.9 ± 0.78 | — |
| GK44 | 11.5 ± 1.43 | — |
| SCRC28 | 8.0 ± 1.90 | — |

Note:
"—" indicates no comparison was made.

The results showed that there were no significant differences in terms of the numbers of boll setting in individual plant between cotton variety sGK9708-41 and the genetically modified cotton containing empty-vector. The numbers of boll setting in individual plant of the genetically modified cotton lines containing VdAL were each higher than the numbers of boll setting in individual plant of the wildtype cotton variety sGK9708-41. The numbers of boll setting in individual plant of genetically modified cotton lines P1-89, P1-96, P1-117, P1-90, P1-84, P1-134, P1-143, P1-109, P1-105, P1-76, P1-82, P1-136, P1-100, P1-127, P1-135, P1-102, P1-80, P1-104, P1-69, P1-110, and P1-111, containing VdAL, were each higher than the numbers of boll setting in individual plant of high-yield cotton variety SCRC28 also. The numbers of boll setting in individual plant of some lines (such as P1-96, P1-117, P1-82, P1-100, P1-127, P1-102, P1-80, P1-104, and P1-69) were each higher even than the numbers of boll setting in individual plant of *Verticillium* wilt resistant cotton variety GK44.

The results showed that the VdAL of the present invention could enhance *Verticillium* wilt resistant ability of a plant and reduce the effect of *Verticillium* wilt on cotton yield.

Example 2

In this example, it was proved that VdAL protein associated with disease resistance could enhance disease resistance of *Arabidopsis thaliana*.

I. Construction of the Genetically Modified *Arabidopsis thaliana* Containing VdAL Procedure 1 Constructions of a Recombinant Vector and a Recombinant Strain A DNA molecule shown in nucleotides 1-792 of SEQ ID NO: 2 in the Sequence Listing, i.e., VdAL protein gene associated with disease resistance, was artificially synthesized. A sequence between recognition sites of Pst I and Kpn I of vector pCAMBIA1300-Super was replaced with the DNA molecule shown in nucleotides 1-792 of SEQ ID NO: 2 in the Sequence Listing (i.e., the VdAL protein gene associated with disease resistance), and other sequences of pCAMBIA1300-Super remained unchanged, to obtain a recombinant vector named pCAMBIA1300-Super-VdAL. Recombinant vector pCAMBIA1300-Super-VdAL expresses the protein shown in SEQ ID NO: 1 in the Sequence Listing.

SEQ ID NO: 2 consists of 864 nucleotides, encoding an amino acid sequence shown in SEQ ID NO: 1. Nucleotides 793-864 of SEQ ID NO: 2 encode FLAG shown in amino acids 265-287 of SEQ ID NO: 1; and nucleotides 1-792 of SEQ ID NO: 2 encode a protein shown in amino acids 1-264 of SEQ ID NO: 1.

pCAMBIA1300-Super-VdAL was introduced into *Agrobacterium tumefaciens* GV3101, to obtain a recombinant strain, which was named A-pCAMBIA1287-Super-VdAL.

pCAMBIA1300-Super was introduced into *Agrobacterium tumefaciens* GV3101, to obtain a recombinant strain with an empty vector, and the resulting recombinant strain was named A-pCAMBIA1300-Super.

Procedure 2 Construction of Disease Resistance Related VdAL Protein Genetically Modified *Arabidopsis thaliana*

In step (1), recombinant strain A-pCAMBIA1300-Super-VdAL of procedure 1 was streaked on a YEB solid medium containing kanamycin with a final concentration of 50 µg/mL and rifampicin with a final concentration of 50 µg/mL, activated, and cultured for 48 h at 28° C., to obtain single colonies.

In step (2), some single colonies obtained in step (1) were selected and added into a 5 mL of YEB liquid medium containing kanamycin with a final concentration of 50 µg/mL and rifampicin with a final concentration of 50 µg/mL, and shaken for 12 h at 28° C., to obtain a bacterial solution.

In step (3), 2 mL of the bacterial solution obtained in step (2) was inoculated to a 500 mL of YEB liquid medium containing kanamycin with a final concentration of 50 µg/mL and rifampicin with a final concentration of 50 µg/mL, shaken on a shaking table at 28° C., and cultured to OD600=0.8-1.0, to obtain a bacterial solution.

In step (4), the bacterial solution obtained in step (3) was centrifuged at 4000 rpm for 10 minutes at room temperature, to obtain a bacterial precipitate.

In step (5), the bacterial precipitate obtained in step (4) was re-suspended in 200 mL of ½ MS solution, in which 15 µL of Silwet-77 was added, followed by homogeneous mixing, to obtain an *Agrobacterium tumefaciens* infection solution.

In step (6), flowers of *Arabidopsis thaliana* Col in a flowering stage were immersed in the *Agrobacterium tumefaciens* infection solution obtained in step (5) for 30 sec, and then taken out, and cultured at room temperature for 24 h in the darkness, to obtain infected *Arabidopsis thaliana*.

Figure 3:
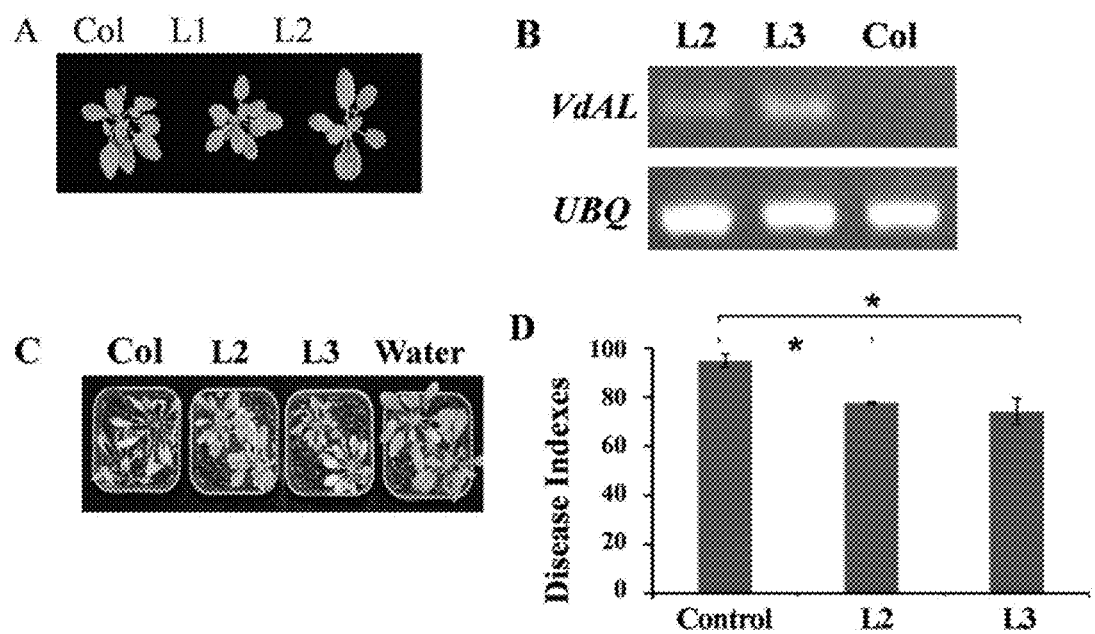
FIG. 3 shows resistance ability to *Verticillium* will of the genetically modified *Arabidopsis thaliana* containing VdAL, wherein A represents genetically modified *Arabidopsis thaliana* lines 2 and 3, containing VdAL, of a T3 generation; B represents the transcription levels of VdAL gene in genetically modified *Arabidopsis thaliana* lines 2 and 3, containing VdAL, of the T3 generation identified by semi-quantitative PCR; C indicates the growth status of genetically modified *Arabidopsis thaliana* lines 2 and 3, containing VdAL, of the T3 generation after inoculation of cotton *Verticillium dahlia*; and D shows the disease indexes of genetically modified *Arabidopsis thaliana* lines 2 and 3, containing VdAL, of the T3 generation.

In step (7), the infected *Arabidopsis thaliana* obtained in step (6) was cultured at room temperature for 24 h under low light, and then cultured at 22° C. under 16 hours of illumination/8 hours of darkness light cycle. Such a plant was a genetically modified plant of $T_0$ generation. The genetically modified plant was passaged to T3 generation (by selfing in each generation). Each generation was screened with hygromycin, to obtain lines 2 and 3 of genetically modified *Arabidopsis thaliana*, containing VdAL, of the T3 generation (see A in FIG. 3).

In step (8), VdAL gene in the lines 2 and 3 of the genetically modified *Arabidopsis thaliana* of, containing VdAL, the T3 generation obtained in step (7) was identified at a genomic level. *Arabidopsis thaliana* Col was used as a wildtype reference, with a primer pair of ATGCTTTCTCTCCAGACCGCAGC (SEQ ID NO: 13) and TAGCGCAGTTACGATCAGGGTCG (SEQ ID NO: 14). Results showed that PCR products of the lines 2 and 3 both had target bands of size 403 bp, indicating that the lines 2 and 3 both had VdAL gene.

In step (9), expression of the VdAL gene in the lines 2 and 3 of the genetically modified *Arabidopsis thaliana*, containing VdAL, of the T3 generation obtained in step (7) was identified by semi-quantitative PCR. *Arabidopsis thaliana*

Col was used as a wildtype reference, with a primer pair of GCAACATCACCCTTCGTACT (SEQ ID NO: 15) and CAGACTGGTTGCCGAAGAA (SEQ ID NO: 16). UBQ was used as an internal reference, with a primer pair of CCCTGGCTGATTACATC (SEQ ID NO: 11) and TGGTGTCAGTGGGTTCAATG (SEQ ID NO: 12) (see B in FIG. 3). Results showed that PCR products of the lines 2 and 3 both had target bands, indicating that the lines 2 and 3 both expressed the VdAL gene.

Figure 4:
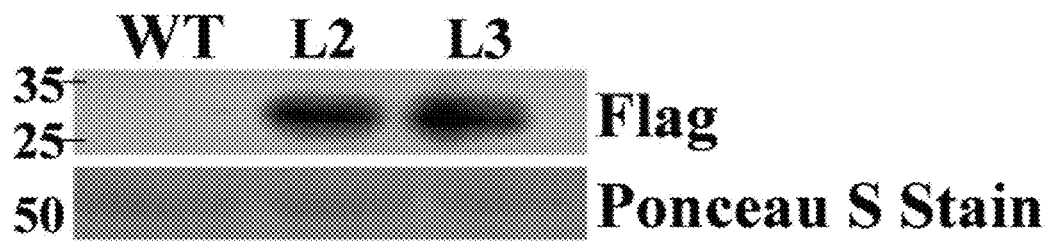
FIG. 4 shows western blot identification of VdAL protein expressed in genetically modified *Arabidopsis thaliana* lines 2 and 3, containing VdAL, of the T3 generation.
Figure 5:
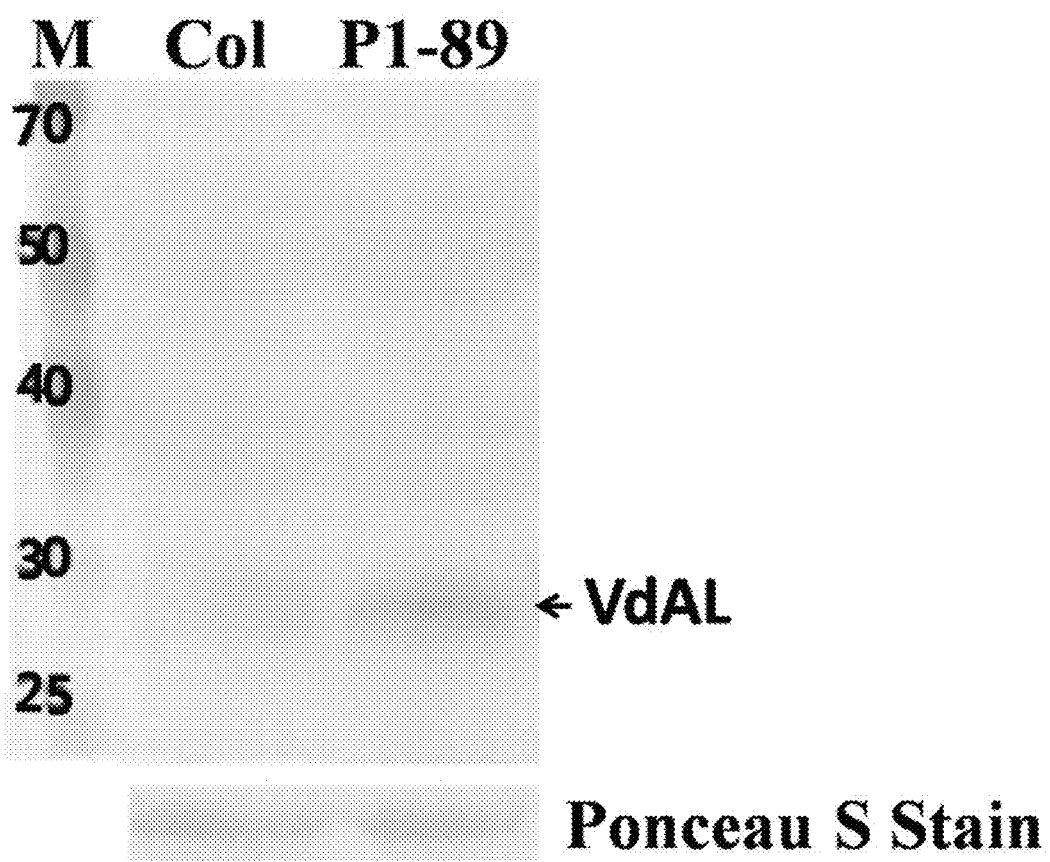
FIG. 5 shows western blot detection results of VdAL gene in genetically modified cotton lines P1-89, containing VdAL.

In step (10), expression of VdAL protein in the lines 2 and 3 the genetically modified Arabidopsis thaliana, containing VdAL, of the T3 generation obtained in step (7) was identified by western-blot. Arabidopsis thaliana Col was used as a wildtype reference. Antibody flag (item number AB003-01A, a product of Shanghai Nearshore Technology Co. LTD/Sinobio Biotech Co., Ltd.) was used. Protein was labeled with a Ponceau S dyeing solution, and a loading amount was adjusted, to enable a same total protein amount in different lanes. Results were shown in FIG. 4. The results indicated that the lines 2 and 3 both expressed the VdAL protein.

A-pCAMBIA1300-Super-VdAL was replaced with A-pCAMBIA1300-Super according to steps (1) to (7), and other steps were unchanged. Genetically modified Arabidopsis thaliana with an empty vector was obtained and named genetically modified Arabidopsis thaliana containing empty-vector.

II. Identification of Disease Resistance of the Genetically Modified Arabidopsis thaliana Containing VdAL The genetically modified Arabidopsis thaliana containing VdAL was inoculated with Verticillium dahliae, and disease resistance of a plant after inoculation was evaluated by Verticillium wilt index of the plant. The experiment was repeated three times, including the following specific steps each time.

Spores of Verticillium dahliae were suspended in sterile distilled water, to obtain a spore suspension at a concentration of $1 \times 10^6$ cfu/mL. The line 2 of the genetically modified Arabidopsis thaliana containing VdAL obtained in step (1) was soaked in the spore suspension for 30 s and then cultured at 22° C. under a 16 hours of illumination/8 hours of darkness light cycle for 21 days, to obtain treated line 2, altogether 30 plants.

The line 2 of the genetically modified Arabidopsis thaliana containing VdAL of step (1) was replaced with the line 3 of the genetically modified Arabidopsis thaliana containing VdAL of step (1), Col, and the genetically modified Arabidopsis thaliana containing empty-vector obtained in step (1), respectively, and the other steps were unchanged, to obtain treated line 3, treated Col, and treated the genetically modified Arabidopsis thaliana containing empty-vector, respectively.

The strain 2 of the genetically modified Arabidopsis thaliana containing VdAL of step (1) was replaced Col, a non-genetically modified control, and the spore suspension was replaced with sterile distilled water, the other steps remaining unchanged, to obtain the control line, Col dipped in water.

Disease indexes (see C and D in FIG. 3) of the treated line 2, the treated line 3, the treated Col, the treated the genetically modified Arabidopsis thaliana containing empty-vector, and the reference Col dipped in water were counted according to the following criteria, respectively:

Grade 0: no diseased leaves;
Grade I: 0.1%-25% of diseased leaves;
Grade II: 25% (excluded)-50% of diseased leaves;
Grade III: 50% (excluded)-75% of diseased leaves; and
Level IV: more than 75% of diseased leaves.

Disease indexes were calculated according to the following formula: disease index=[Σdisease grades×plant number/(total plant number×highest disease grade)]×100.

The results showed that there were no significant differences in terms of disease index between Col and the genetically modified Arabidopsis thaliana containing empty-vector. The disease index of Col was 95±2.6; the disease index of the line 2 was 76±1.6, 80% of that of Col; the disease index of the line 3 was 74±5.4, 78% of that of Col; and the disease index of reference Col dipped in water was 0. The disease indexes of the line 2 and the line 3 were both significantly lower than the disease index of Col. The results showed that VdAL could enhance resistant ability to Verticillium wilt of a plant.

INDUSTRIAL APPLICABILITY

The experiments showed that the VdAL (protein associated with disease resistance) and its encoding gene could enhance a plant's ability to resist Verticillium wilt. Verticillium wilt indexes of the genetically modified cotton lines containing VdAL were each lower than the Verticillium wilt index of wildtype cotton variety sGK9708-41, and also lower than the Verticillium wilt index of high-yield cotton variety SCRC28. The Verticillium wilt indexes of genetically modified cotton lines P1-89, P1-96, P1-117, P1-90, P1-84, and P1-134, containing VdAL, were each lower even than the Verticillium wilt index of Verticillium wilt resistant cotton variety GK44. The relative control effects of the genetically modified cotton lines containing VdAL were each higher than the relative control effect of wildtype cotton variety sGK9708-41, and also higher than the relative control effect of high-yield cotton variety SCRC28. The relative control effects of genetically modified cotton lines P1-89, P1-96, P1-117, P1-90, P1-84, and P1-134, containing VdAL, each reached above 80%, higher even than the relative control effect of Verticillium wilt resistant cotton variety GK44.

VdAL (protein associated with disease resistance) and its encoding gene of the present invention could enhance the ability in a plant to resist Verticillium wilt, and reduce the effect of Verticillium wilt on cotton yield. The numbers of boll setting in individual plant of the genetically modified cotton lines containing VdAL were each higher than the numbers of boll setting in individual plant of the wildtype cotton variety sGK9708-41. The numbers of boll setting in individual plant of genetically modified cotton lines P1-89, P1-96, P1-117, P1-90, P1-84, P1-134, P1-143, P1-109, P1-105, P1-76, P1-82, P1-136, P1-100, P1-127, P1-135, P1-102, P1-80, P1-104, P1-69, P1-110, and P1-111, containing VdAL, were each higher than the numbers of boll setting in individual plant of high-yield cotton variety SCRC28 also. The numbers of boll setting in individual plant of genetically modified cotton lines P1-96, P1-117, P1-82, P1-100, P1-127, P1-102, P1-80, P1-104, and P1-69 containing VdAL were each higher even than the numbers of boll setting in individual plant of Verticillium wilt resistant cotton variety GK44.

The experiments showed that the VdAL (protein associated with disease resistance) and its encoding gene of the present invention could be used to enhance disease resistance of a plant.

The invention claimed is:

1. A protein of a) or c) as follows:
   a) the protein having an amino acid sequence as shown in amino acids 1-264 of SEQ ID NO: 1; and
   c) the protein having an amino acid sequence as shown in SEQ ID NO: 1.

2. A biomaterial associated with the protein of claim 1, wherein the biomaterial is any one selected from a group consisting of B1) to B22) as follows:
   B1) a nucleic acid molecule encoding the protein of claim 1;
   B2) an expression cassette comprising the nucleic acid molecule of B1);
   B3) a recombinant vector comprising the nucleic acid molecule of B1);
   B4) a recombinant vector comprising the expression cassette of B2);
   B5) a recombinant microorganism comprising the nucleic acid molecule of B1);
   B6) a recombinant microorganism comprising the expression cassette of B2);
   B7) a recombinant microorganism comprising the recombinant vector of B3);
   B8) a recombinant microorganism comprising the recombinant vector of B4);
   B9) a genetically modified plant cell line comprising the nucleic acid molecule of B1);
   B10) a genetically modified plant cell line comprising the expression cassette of B2);
   B11) a genetically modified plant cell line comprising the recombinant vector of B3);
   B12) a genetically modified plant cell line comprising the recombinant vector of B4);
   B13) a genetically modified plant tissue comprising the nucleic acid molecule of B1);
   B14) a genetically modified plant tissue comprising the expression cassette of B2);
   B15) a genetically modified plant tissue comprising the recombinant vector of B3);
   B16) a genetically modified plant tissue comprising the recombinant vector of B4);
   B17) a genetically modified plant organ comprising the nucleic acid molecule of B1);
   B18) a genetically modified plant organ comprising the expression cassette of B2);
   B19) a genetically modified plant organ comprising the recombinant vector of B3);
   B20) a genetically modified plant organ comprising the recombinant vector of B4);
   B21) a genetically modified plant comprising the nucleic acid molecule of B1); and
   B22) a genetically modified plant comprising the expression cassette of B2).

3. The biomaterial according to claim 2, wherein the nucleic acid molecule of B1) is a gene represented by:
   1) a cDNA or DNA molecule having a nucleotide sequence as shown in nucleotides 1-792 of SEQ ID NO: 2; or 4) a cDNA or DNA molecule having a nucleotide sequence as shown in SEQ ID NO: 2.

4. A method for
a) regulation of plant disease resistance; or
b) cultivation of a disease-resistant genetically modified plant,
which comprises utilizing the protein of claim 1.

5. The method according to claim 4, wherein the plant is a dicotyledonous or monocotyledonous plant.

6. The method according to claim 4, wherein the disease resistance is *Verticillium* wilt resistance.

7. The method according to claim 4, wherein the plant is a dicotyledonous plant or a monocotyledonous plant, and the disease resistance is *Verticillium* wilt resistance.

8. A method for cultivating a disease-resistant genetically modified plant, comprising a step of introducing a gene encoding the protein of claim 1 into a recipient plant, to obtain the disease-resistant genetically modified plant having stronger disease resistance than the recipient plant.

9. The method according to claim 8, wherein the gene encoding the protein of claim 1 is a DNA molecule having an encoding sequence as shown in nucleotides 1-792 of SEQ ID NO: 2.

10. The method according to claim 8, wherein the plant is a dicotyledonous plant and/or a monocotyledonous plant.

11. The method according to claim 8, wherein the disease resistance is *Verticillium* wilt resistance.

12. The method according to claim 8, wherein the gene encoding the protein of claim 1 is a DNA molecule having an encoding sequence as shown in nucleotides 1-792 of SEQ ID NO: 2, and the plant is a dicotyledonous plant and/or a monocotyledonous plant.

13. The method according to claim 8, wherein the gene encoding the protein of claim 1 is a DNA molecule having an encoding sequence as shown in nucleotides 1-792 of SEQ ID NO: 2, and the disease resistance is *Verticillium* wilt resistance.

14. The method according to claim 8, wherein the plant is a dicotyledonous plant and/or a monocotyledonous plant, and the disease resistance is *Verticillium* wilt resistance.

15. The method according to claim 8, wherein the gene encoding the protein of claim 1 is a DNA molecule having an encoding sequence as shown in nucleotides 1-792 of SEQ ID NO: 2;
the plant is a dicotyledonous plant and/or a monocotyledonous plant; and
the disease resistance is *Verticillium* wilt resistance.

* * * * *